(12) United States Patent
Su (10) Patent No.: US 8,603,510 B2
(45) Date of Patent: *Dec. 10, 2013

(54) SEMIOCHEMICAL RESERVOIR TO ATTRACT SUBTERRANEAN TERMITES TUNNELING IN SOIL

(75) Inventor: Nan-Yao Su, Davie, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1870 days.

This patent is subject to a terminal disclaimer.

(21) Appl. No.: 11/638,154

(22) Filed: Dec. 13, 2006

(65) Prior Publication Data

US 2007/0092548 A1    Apr. 26, 2007

Related U.S. Application Data

(62) Division of application No. 10/392,798, filed on Mar. 19, 2003, now Pat. No. 7,169,403.

(60) Provisional application No. 60/366,830, filed on Mar. 22, 2002.

(51) Int. Cl.
*A01N 25/10*    (2006.01)

(52) U.S. Cl.
USPC ............ 424/410; 43/132.1; 424/84; 424/405; 424/406; 424/409; 424/DIG. 11; 523/122

(58) Field of Classification Search
None
See application file for complete search history.

(56) References Cited

U.S. PATENT DOCUMENTS

| | | |
|---|---|---|
| 3,070,495 A | 12/1962 | Esenther et al. |
| 3,858,346 A | 1/1975 | Bailey |
| 4,043,073 A | 8/1977 | Basile |
| 4,363,798 A | 12/1982 | D'Orazio |
| 4,455,441 A | 6/1984 | Prestwich |
| 5,024,832 A | 6/1991 | Omata et al. |
| 5,141,744 A | 8/1992 | Chang et al. |
| 5,142,817 A | 9/1992 | Rolf |
| 5,151,443 A | 9/1992 | Henrick |
| 5,173,535 A | 12/1992 | Abrutyn |

(Continued)

FOREIGN PATENT DOCUMENTS

| | | |
|---|---|---|
| JP | 62 177040 | 1/1989 |
| JP | 03 112903 A | 5/1991 |

(Continued)

OTHER PUBLICATIONS

Su et al Remidial Baiting with Hexaflumuron—J. of Economic Entomology 1997, 90,(3) ,809-817.*

(Continued)

*Primary Examiner* — Neil Levy
(74) *Attorney, Agent, or Firm* — Saliwanchik, Lloyd & Eisenschenk (57) ABSTRACT

The present invention relates generally to polymer devices impregnated with semichemical attractants for termites. The materials for delivering the semiochemicals are preferably cellulose-free. Devices of the subject invention are placed in soil and provide a slow-release and permeation of the semiochemicals into the adjacent soil so that termites tunneling in the vicinity are directed toward the chemical sources. Because the semiochemicals are impregnated in the polymer, the device also protects the semiochemicals so that they do not degrade rapidly under field conditions. In a preferred embodiment, the subject invention comprises a durable station housing, preferably with a removable bait, wherein the body of the station housing itself is impregnated with a semiochemical attractant.

14 Claims, 2 Drawing Sheets

(56) References Cited

U.S. PATENT DOCUMENTS

| | | | |
|---|---|---|---|
| 5,504,142 | A | 4/1996 | Caupin et al. |
| 5,571,967 | A | 11/1996 | Tanaka et al. |
| 5,572,825 | A | 11/1996 | Gehret |
| 5,573,760 | A | 11/1996 | Thorne et al. |
| 5,609,879 | A * | 3/1997 | Myles ............ 424/410 |
| 5,637,298 | A | 6/1997 | Stowell |
| 5,874,097 | A | 2/1999 | Henderson et al. |
| 5,899,018 | A | 5/1999 | Gordon et al. |
| 5,921,018 | A | 7/1999 | Hirose et al. |
| 5,927,001 | A | 7/1999 | Ballard et al. |
| 6,023,879 | A | 2/2000 | Katz et al. |
| 6,058,646 | A | 5/2000 | Bishoff et al. |
| 6,079,151 | A | 6/2000 | Bishoff et al. |
| 6,093,389 | A | 7/2000 | Galinis et al. |
| 6,100,805 | A | 8/2000 | Lake |
| 6,158,166 | A | 12/2000 | Snell et al. |
| 6,203,811 | B1 | 3/2001 | McPherson et al. |
| 6,216,960 | B1 | 4/2001 | Aiba et al. |
| 6,857,223 | B2 * | 2/2005 | Su ............ 43/131 |
| 2001/0001236 | A1 | 5/2001 | Lake |
| 2002/0046483 | A1 * | 4/2002 | Snell et al. ............ 43/131 |

FOREIGN PATENT DOCUMENTS

| | | | |
|---|---|---|---|
| JP | 57 139005 | | 8/1992 |
| JP | 06211614 | * | 8/1994 |
| JP | 2000 239114 A | | 9/2000 |
| JP | 2001-327237 A | | 11/2001 |
| WO | WO 93/23998 | | 12/1993 |

OTHER PUBLICATIONS

Sekamatte, et al The Potential of Protein- and Sugar-Based Baits to Enhance Predatory Ant Activity and Reduce Termite Damage—Crop Protection (2001), 20,(8), 653-662.*

Rust, M.K., et al., "Enhancing Foraging of Western Subterranean Termites (Isoptera: Rhinotermitidae) in Arid Environments," Sociobiology (1996), pp. 275-286, vol. 28, iss. 3.

Cornelius, M.L. et al., "Responses of *Coptotermes formosanus* and . . . ," Journal of Economic Enotmology (Feb. 20, 2002), pp. 121-128, vol. 95, No. 1 (abstract).

Grace, J.K. et al., "Trail-following behavior of *Reticulitermes hesperus* Banks Isoptera . . . ," Journal of Chemical Ecology (1998), pp. 653-668, vol. 14, No. 2 (abstract).

Reinhard, J. et al., "Trail communication during foraging and recruitment in the . . . ," Journal of Insect Behavior (Mar. 2001), pp. 157-171, vol. 14, No. 2 (abstract).

Matsumura, F. et al., "Influence of carbon sources on the production of the termite . . . ," Journal of Chemical Ecology (1976), pp. 299-305, vol. 2, No. 3 (abstract).

* cited by examiner

SEMIOCHEMICAL RESERVOIR TO ATTRACT SUBTERRANEAN TERMITES TUNNELING IN SOIL

CROSS-REFERENCE TO RELATED APPLICATION

This application is a divisional of U.S. Ser. No. 10/392,798, filed Mar. 19, 2003, now U.S. Pat. No. 7,169,403 currently allowed, which claims the benefit of U.S. Provisional Application No. 60/366,830, filed Mar. 22, 2002.

BACKGROUND OF THE INVENTION

One relatively recent development in termite control is the use of slow-acting toxicants for managing subterranean termite populations near structures. Many chemical "attractants" (pheromones and the like) have been proposed for use in such baits. See, e.g., WO 93/23998 and U.S. Pat. No. 5,571,967. However, there have been few if any demonstrations of true "attraction" of subterranean termites that forage in soil. The term "attractant" is often confused with or misused in place of "feeding stimulant," or "arrestant" (which are chemical cues that cause the animals to aggregate near the chemical source). An "attractant" is "a chemical that causes animals to make orientated movement toward its sources" (Shorey, 1977). Semiochemicals are chemical substances that deliver behavioral messages to animals (Metcalf & Metcalf, 1975).

There are many patents that refer to the use of feeding stimulants in cellulose-based baits to increase termite feeding on baits. Some of the patents refer to "attractants," but the data and proposed uses indicate that they actually involve "feeding stimulants" that increase termite feeding on baits rather than attractants that cause termites to "make orientated movement toward its sources." For example, U.S. Pat. No. 6,093,389 relates to a steroid derivative in a cellulose-based termite bait. This reference states that the use of decayed or fungus-inoculated wood to attract termites is not satisfactory for commercial use. A food source is said to be an important component in the bait compositions of this patent.

U.S. Pat. No. 5,874,097 relates to the use of chemicals (naphthalene and others similar to nest extracts; identified in PAPERMATE ball-point pens that were found to elicit trail-following behavior in termites) to increase termite feeding on baits comprising cardboard, paper, sugar cane, corn cobs, and other cellulose mixtures. U.S. Pat. No. 5,637,298 uses 2-naphthalenemethanol in cellulose-based baits such as cardboard and paper to induce trail-following behavior and for feeding stimulation to increase the rate of bait consumption by termites. U.S. Pat. No. 3,858,346 uses "termite-attracting" carbohydrate (hexachlorocyclo-pentadiene dimer) in sawdust-based bait to increase termite feeding of baits.

Rust et al., *Sociobiology*, Vol. 28, No. 3, pp. 275-285 (1996), discuss attempts to use extracts of brown-rot fungus to increase the likelihood that wood stakes would be located by termites. Water was used in an attempt to disperse the extract in sand. It was noted that the extract was not soluble enough in water, and surfactants were used in an attempt to improve the effective depth that the fungal extract would penetrate the soil. Field studies of sweetgum blocks conditioned with the *Gloeocphyllum trabeum* fungus "did not reveal any special attractiveness." The conclusion of this reference was that additional research is needed to insure the longevity and maximal dispersion of such attractants in soil.

U.S. Pat. No. 6,203,811 uses a fungal extract as a "feeding stimulant" in cellulose-based baits to increase termite feeding on the baits.

Various patents relate to the feeding stimulants in wood blocks together with a slow-acting insecticide. Again, some of these patents might use the term "attractant," but the data and proposed use indicate they do not and are not intended to "cause termites to make orientated movement toward its sources." Thus, these are examples of "feeding enhancers." U.S. Pat. No. 4,455,441 uses an "attractant termiticide" compound in a feeding block. U.S. Pat. No. 3,070,495 places wood blocks treated with fungi-decay extract and an insecticide in the ground; this might result in increased termite feeding but did not "attract" subterranean termites from any distance. U.S. Pat. No. 4,363,798 uses fungi-decayed wood blocks impregnated with borons (to kill termites).

In most or all of the art mentioned above, feeding stimulants or other "attractive" semiochemicals are incorporated in toxic baits, which are not intended for "monitoring." U.S. Pat. No. 5,573,760 teaches a composition "preferred" by termites that is to be used for monitoring termites in soil before toxicant baits are installed. The data showed that the medium was "highly palatable" but did not demonstrate that it caused termites foraging in soil "to make orientated movement toward its sources." Thus, that medium functioned as a feeding stimulant rather than as an "attractant." The following portion from that patent clearly illustrates the difference between "attractants" and feeding stimulants:

> It is important to note that the monitoring composition does not attract termites per se. One would not want to attract termites and create a problem where none existed before. However, because termites prefer consuming the monitoring composition, once the termites discover it, they will return to it and recruit others from the colony. Subterranean termites tunnel underground and will tunnel into the monitoring composition. The termites will stimulate other colony members to use the food, then return to the colony and share the food. These behavioral patterns are utilized to great advantage in the monitoring and controlling methods of the present invention.

Consistent with this, the art heretofore taught that a cellulose-based food source was an essential element to make the baits sufficiently "attractive" to termites (even if pheromone "attractant" is also used). While the art mentions the use of pheromones to make baits more attractive, the art generally teaches that a cellulose/food source is needed in conjunction with the pheromone. U.S. Pat. No. 5,151,443 mentions that trail pheromones and decayed wood can be used with sawdust and the like in baits for controlling termites. U.S. Pat. No. 6,100,805 relates to a spike-shaped tube for termite detection. A conductive loop is present between two wooden blocks inside the tube. A pheromone can be formed over or blended within "electrically insulative protective material" that covers the conductive loop. The insulation can be a resin such as an epoxy resin, including two-part epoxy resins. However, the wooden blocks are treated as essential components. Apparently, a cellulose food source was deemed to be essential as an "attractant." U.S. Pat. No. 5,571,967 relates to a termite-detecting electronic device. The device as illustrated has a can-like outer "casing" that is to be positioned primarily above ground. A wooden detecting sample (a cube of wood) is within the "casing." As the detecting block is degraded, presumably by termites, such movement is detected by the electronic apparatus. The '967 patent states that a termite-guiding pheromone is used in order to "attract" termites to the detecting sample.

However, one major obstacle to the successful "real world" use of cellulose-based medium or baits that are placed in soil is their relatively short life. Thus, these references do not even identify a main problem with pheromones and cellulose-based baits: especially when used in hot and humid soil, the chemical attractants therein decompose too quickly to be of practical use for "attractant" delivery. It would be particularly advantageous to have monitoring devices that would last after eliminating the structure-infesting populations by the initial baiting, in which months or years may pass before new populations of subterranean termite migrate near the stations. Under these circumstances, an "attractant" would need to remain available in soil for months and sometimes years.

For commercial monitoring-baiting programs, the monitoring devices may have to remain in soil for 6-18 months before termites are detected in the stations. Most commercial baiting programs, such as the SENTRICON® Termite Colony Elimination System, involve a monitoring-baiting procedure that depends on the monitoring phase to detect termites before toxic baits are used.

There are other issues to be addressed in order to successfully use pheromones and baits. For example, U.S. Pat. No. 5,572,825 relates to a glue trap primarily for trapping cockroaches and the like. This patent acknowledges that aggregation pheromones might be used but notes that there are associated difficulties, such as identifying and characterizing a desired pheromone (which can be colony-specific) and maintaining the stability of such volatile hormones.

WO 93/23998 mentions the use of bait materials such as METHOCEL in a casing in a station housing. This application also states that pheromones (and the like) can be used to modify the monitoring device to increase the possibility that the target pest will enter and move within the device. However, it is also noted therein that trail pheromones can actually cause foraging termites to avoid eating the bait, and that reproducing functional synthetic pheromones can be very difficult (especially in light of the observation that different pheromones can be pest and colony specific).

U.S. Pat. No. 5,024,832 showed that the (3Z, 6Z, 8E)-dodecatrienol has a unique characteristic of inducing termite trail-marking. The embodiment described therein involved detecting and capturing foraging termites by placing a glass plate coated with this trail-marking pheromone on the surface of the soil. As with many behavior-modifying semiochemicals, however, (3Z, 6Z, 8E)-dodecatrienol is unstable in soil or in open air (as it reacts with oxygen). It thus degrades too quickly for practical use.

U.S. Pat. Nos. 6,079,151 and 6,058,646 discuss in more detail the species- and colony-specific nature of pheromones, as well as the difference between trail and feeding-initiating pheromones. The embodiments illustrated in these patents appear to be above-ground boxes for mounting to a structure. These patents state that pheromone mimics can make the matrix attractive or non-repellent to the pest species being monitored or controlled.

Some attempts have been made to attract termites without pheromones. U.S. Pat. No. 6,023,879 describes a device to deliver water in soil near bait stations to attract termites. U.S. Pat. No. 5,921,018 teaches an elaborate apparatus to collect and channel rainwater in soil near bait stations to capture and kill termites. U.S. Pat. No. 5,899,018 describes a device that uses the solar heating/night cooling cycle to deliver a moisture-absorbing "attractant" (cardboard, cow dung, wood, and the like) into soil to attract termites. On the other hand, U.S. Pat. No. 5,927,001 relates to a bait station having a tubular body (made of rigid foam or plastic like Styrofoam) with a triangular cross section; a triangular bait is fitted into the bait holder. The bait holder is designed to keep water away from the cardboard to prevent its degradation. The bait is impregnated with a toxicant. Pheromones are not mentioned in this patent.

U.S. Pat. No. 6,158,166 includes a discussion of materials that can be used as termite bait. Rigid foam such as Styrofoam is one suggestion. However, it is clearly noted therein that such materials are not actual food sources and thus are to be used in conjunction with natural wood products.

U.S. Pat. No. 4,043,073 relates to a container that encloses bait material for termites or other pests, wherein the bait has an odiferous material in it to signal to humans when the container has been attacked by pests. This patent mentions that a hormone can be added as an attractant to the container wall. These containers appear to be "permanently" buried in the ground without having the bait replaced. This patent does not teach or suggest the combination of advantages that using a pheromone in a SENTRICON-like housing would provide. While this patent, like many others, mentions hormones, this patent does not show any actual success of doing so.

U.S. Pat. No. 5,141,744 relates to a macrogel that can be in the form of a cone, funnel, tube, or spike wherein the macrogel contains an entomopathogen attractant such as fungal-decayed wood. U.S. Pat. No. 5,504,142, entitled "Device for Controlling Insects," relates to a mixture comprising a thermoplastic elastomer and at least one chemical mediator (including pheromones) that acts on the behavior of insects and acarids. The invention is designed for treating crops against insects and acarids. The mixture can take the form of granules or sticks.

The '142 patent cites Japanese Application 81 JP-024042, published as KOKAI JP 57 139005, as describing compositions of pheromones and of a binder containing 4 to 20% of pheromones. The binder is silicone or SBR rubber. A solvent such as methylene chloride, benzene, an alcohol, etc. and fillers such as cellulose, silica, active carbon, or carbonate are also used. The product is in paste form.

The '142 patent also cites U.S. Pat. No. 5,142,817 as describing sheets or strips formed of a sheet of water-insoluble polymer adhesively bonded to a sheet of a hydrophilic matrix. This matrix may be made of cellulose fibers, polyester, polyacetate, polyvinyl alcohol, or polyoxyethylene glycol. This matrix contains a plasticizer such as polyoxyethylene glycol or a sorbitol solution and also a biologically active product. These strips serve to envelop trees. The biologically active product is released by a humid atmosphere and serves to protect the trees. The biologically active products are stated therein to include pheromones.

Unlike terrestrial insects that live above ground (and can thus orient themselves using chemical cues that disperse at a distance in the atmosphere), termites tunnel underground in soil. Chemicals do not move as freely (if at all) in soil as they do in the atmosphere. Much prior art relates to the release of vapor phase pheromones into atmosphere, but vapor does not travel at any significant distance in soil where subterranean termites tunneling activity occurs. If a true "attractant" is to be developed for practical use, there is a need to deliver "attractive" agents into the soil so that they cause termites, when present, to "make orientated movement toward its sources." For example, U.S. Pat. No. 6,216,960 relates to a sustained release pheromone dispenser. This device is intended to disperse synthetic sex pheromones into the air to control harmful (flying) insects by disturbing their copulative communication.

Japanese Patent Application No. 62-177040 (publication no. 64-020853) relates to thermoplastic resin powder and cellulose powder impregnated with "a volatile substance." The compositions of this application are designed to effect the gradual release of the "volatile substance."

U.S. Pat. No. 5,173,535 (Dow Corning) relates to plastic materials having particles of crosslinked polymers distributed therein, which entrap functional materials for the purpose of a controlled release of the functional material. The functional materials can include fragrances, pharmaceuticals, dyes, biocides (such as contraceptives), pigments, pesticides, pheromones, and insect repellants. This reference does not relate specifically to controlling termites.

There is no prior suggestion in the art that pheromones could be advantageously incorporated in the housing of a bait station to attract subterranean termites foraging in soil. Furthermore, the art does not provide materials that are impregnated with semiochemicals to permit their release into the soil in adequate amounts for extended periods of time while being exposed to a range of environmental conditions.

BRIEF SUMMARY OF THE INVENTION

The present invention relates generally to polymer devices impregnated with (a high concentration of) a semiochemical attractant for termites. The materials for delivering the semiochemicals are preferably cellulose-free.

Devices of the subject invention are placed in soil and provide a slow-release and permeation of the semiochemicals into the adjacent soil so that termites tunneling in the vicinity are directed toward the chemical sources. Any semiochemicals that can be impregnated into the polymer for any such purposes are included in this invention. However, those with greater water-solubility are preferred so that they can permeate out of the polymer reservoir into soil by soil moisture or free water. The subject invention effectively creates a gradient of semiochemicals in soil and thereby causes termites "to make orientated movement toward its sources." Thus, the subject invention provides a device that can truly deliver "attractants."

Because the semiochemicals are impregnated in the polymer, the device also protects the semiochemicals so that they do not degrade rapidly under field conditions. The subject invention thus enables the chemical gradient to persist in soil for sufficient time so that devices of the subject invention can be used for practical monitoring programs. Termites in the immediate vicinity follow the gradient to the bait, which can include SENTRICON-like stations.

In a preferred embodiment, the subject invention comprises a durable station housing, preferably with a removable bait (a bait that can be removed without substantially disturbing termite foraging tunnels that lead to the bait), wherein the body of the station housing itself is impregnated with a semiochemical attractant. Such arrangements help termites in the immediate area to encounter the bait station to facilitate earlier detection of such termites. Materials ideally suited for use according to the subject invention can be selected in light of this disclosure. While impregnated station housings are one preferred embodiment, various other embodiments are exemplified herein; still others would be apparent to one skilled in the art having the benefit of the subject disclosure. Other examples include sleeves and polymer "chips" that can be placed on and/or near (and/or scattered around) bait stations.

While some prior attempts unsuccessfully tried to use semiochemicals in cellulose/wood baits to stimulate termite feeding (of a toxicant), the subject invention surprisingly and advantageously solves problems associated with using cellulose-based baits. Cellulose was heretofore used in attempts to deliver pheromones to achieve adequate termite congregation and feeding. The subject invention surprisingly departs from the prior teachings, while advantageously (yet counter-intuitively) using materials (heretofore not thought to be possible) that are better suited to deliver sufficient levels of semiochemicals into the soil for extended periods of time. Thus, the subject invention relates generally to the use of cellulose-free materials for delivering pheromones to termites.

The subject invention also provides a novel testing system apparatus. This apparatus enables the identification of semiochemicals that are useful for termite monitoring and control.

DETAILED DESCRIPTION OF THE INVENTION

The present invention describes polymer devices impregnated with (a high concentration of) semiochemical attractants for termites. Devices of the subject invention are placed in soil and provide a slow-release and permeation of the semiochemicals into the adjacent soil so that termites tunneling in the vicinity are directed toward the chemical sources. Because the semiochemicals are impregnated in the polymer, the device also protects the semiochemicals so that they do not degrade rapidly under field conditions.

The pheromone-presenting materials of the subject invention are typically cellulose-free. The subject invention identifies various advantages to using a cellulose-free polymer/plastic instead of impregnated wood or paper. For example, these types of synthetic materials can be impregnated with a higher concentration of the attractant, especially if particularly absorbent materials are selected for this purpose. Cellulose-free materials are also more durable and long-lasting in the environment. Preferred materials are capable of being impregnated with high concentrations of semiochemicals. These and other qualities of the material would allow for long-term dispensation of sufficient amounts of the attractant into the soil. The permeation dynamic is dictated by the concentration of semiochemicals in soil. As the semiochemical concentration in soil declines due to degradation, more semiochemicals will permeate out of the polymer sleeve, and thus maintain the chemical gradient over an extended period.

Figure 1A:
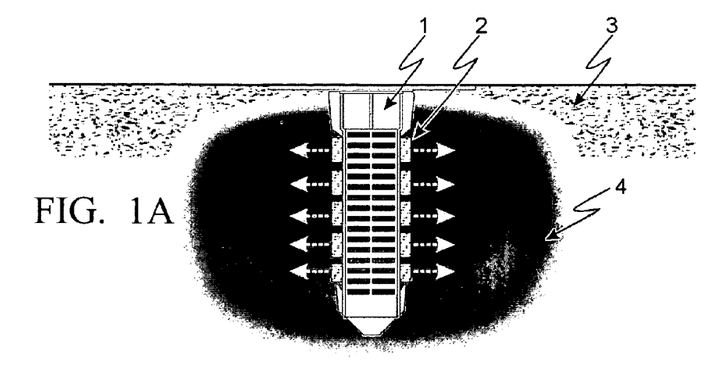
FIG. 1A depicts a monitoring station (1) wrapped with a sleeve (2) of polymer impregnated with an attractant such as fungal-decay extract. Holes are provided on the sleeve to allow termite entry into the station. When buried in soil (3), the attractant permeates into the soil and thus creates a gradient of attractant (4) in the soil adjacent to the station.
Figure 1B:
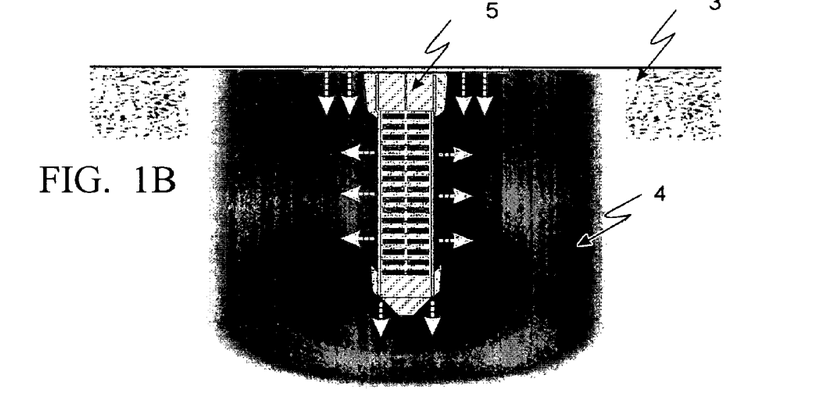
FIG. 1B depicts a monitoring station wherein the housing is impregnated with an attractant such as fungal-decay extract (5).

In a preferred embodiment, as shown in FIG. 1B, the subject invention comprises a durable station housing, preferably with a removable bait, wherein the station housing is impregnated with (or otherwise contains) a semiochemical attractant. The station is made more attractive to termites because the material of the outer housing is impregnated with pheromones and the like. Such arrangements help termites in the immediate area to encounter the bait station to facilitate earlier detection of such termites. Materials ideally suited for use according to the subject invention can be selected for these novel uses. The station housing is preferably durable and sturdy. Preferred station housings are described in WO 93/23998, but materials for the station housing can be optimized for use according to the subject invention.

While impregnated station housings are one preferred embodiment, various other embodiments are exemplified herein, and still others would be apparent to one skilled in the art having the benefit of the subject disclosure. Other examples include sleeves fitted around station housings. Polymer "chips" (preferably disks) can also be attached to, placed near, or scattered around bait stations.

In the preferred embodiment where a polymer impregnated with semiochemicals is used to fabricate the housing of a monitoring station such as the SENTRICON® System, the semiochemicals are protected in the polymer against degradation. Because the entire station is impregnated with the semiochemicals, such embodiments permit a continuous flow of semiochemical to permeate into the adjacent soil ((4) of FIG. 1B). This creates a lasting semiochemical gradient that causes termites, when present, to make oriented movement toward the impregnated stations. Thus, the effective diameter of the bait station is increased. Rather than relying on termites that are already present in an area to encounter the bait station itself, this embodiment of the subject invention presents a bait station with an effective width approaching a foot or so because of the "attractive" gradient.

Station housings of the subject application can be made of a variety of materials, such as porous and/or absorbent plastics and other polymers. The housing could be impregnated with feeding-stimulating and/or congregation pheromones, for example. The pheromone could also be chemically (or otherwise) attached to the station housing instead of, or in addition to, being physically incorporated into the material.

Alternatively, the subject invention also includes a pheromone-laden material attached to (or associated with) a station housing. With reference to FIG. 1A, one such preferred embodiment is a sleeve (with holes) made of one of the above-mentioned polymers (2). When placed over a monitoring station (1) and installed in soil, semiochemicals impregnated in the polymer sleeve permeate into the soil, and thus create a gradient of attractant in the soil adjacent to the station (4). Preferred monitoring stations for use with this embodiment are described in WO 93/23998, for example. Thus, sleeves of the subject invention can be shaped like the station housing (at least the portion of the housing that contacts the ground) and are adapted to fit (snugly) around the housing.

Figure 1C:
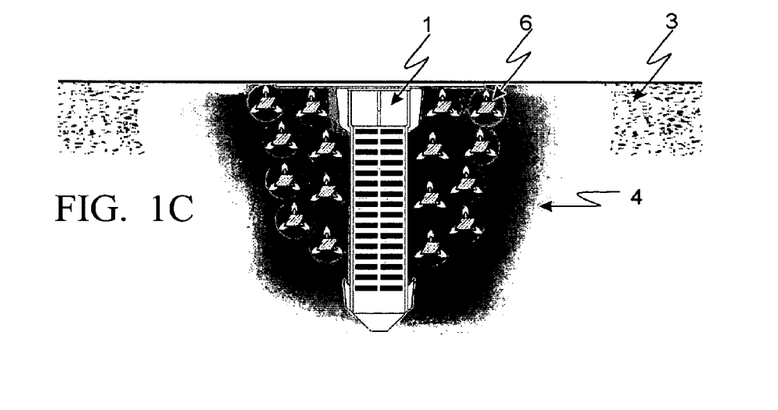
FIG. 1C depicts plastic chips (6), impregnated with an attractant such as fungal-decay extracts, that are buried near a monitoring station so that the attractants are delivered from the chips into the soil near the station.

With reference to FIG. 1C, yet another preferred embodiment is a small polymer chip impregnated with semiochemicals (6). When placed in soil adjacent to a monitoring station (1), semiochemicals would permeate from the chips into the adjacent soil (4), thus creating a lasting semiochemical gradient to attract termites toward the vicinity of the station. Such chips can also be attached to or otherwise associated with a station housing.

In alternative embodiments, the outer-most envelope of the hermetically sealed baits of U.S. provisional application Ser. No. 60/366,380 (filed Mar. 22, 2002; Nan-Yao Su, entitled "Hermetically Sealed Baits for Subterranean Termites") are embedded with the pheromones according to the subject invention. "Chips" of the subject invention can also be scattered near such baits.

Devices of the subject application can be used to target any and all soil dwelling termites, including those of the families Rhinotermitidae and Termitidae. Also "targetable" are termites of the genus *Reticulitermes, Coptotermes, Heterotermes, Odontotermes, Microcerotermes, Amitermes, Macrotermes*, and *Nasutitermes*.

In light of the subject disclosure, it will be recognized that various components can be optimized for particular uses. Thus, the subject invention also includes the related use of specific pheromones, housings made of specific materials, and the use of materials having specific concentrations of the associated pheromone(s).

Candidate semiochemicals for use according to the subject invention include, but are not limited to, known trail-following pheromones such as cis-3, cis-6, trans-8-dodecatrien-1-ol, and related compounds (Matsumura et al. 1969), (3Z, 6Z, 8E)-dodecatrienol, steroid derivatives, 2-naphthalenemethanol, naphthalene and other termite nest extracts, fungi-decayed wood extract, sugars, amino acids, nitrogen-rich substances such as uric acid, carbohydrates such as hexachlorocyclopentadiene dimers, and others. Polymeric devices of the subject invention can also be used to absorb/hold feeding stimulants or arrestants, if desired.

Any semiochemicals that can be impregnated into the polymer for any such purposes are included in this invention. To facilitate movement of semiochemicals by soil moisture or free water, however, water-soluble semiochemicals or their hydrophilic forms are preferred. A preferred embodiment of this invention uses soil moisture or water as a carrier, and thus semiochemicals with high water solubility are preferred candidates for impregnation in the polymer reservoir. Examples of such include but are not limited to sugars or amino acids, or hydrophilic forms of low water-soluble semiochemicals. Because hydrophilic semiochemicals are favored, preferred polymers of the subject invention have a more porous structure than a typical polymer material. These may include, but are not limited to, high absorbent meltblown polypropylene, filament polyester, polyurethane foams with crosslinked nonlinear molecular network, admixture of polymers such as silicones, urethanes, polyurethane, acrylonitrile butadiene and carriers such as clay or amorphous silica.

Most of the behavior-modifying semiochemicals degrade easily under high temperature; thus, special considerations are needed when they are impregnated into the polymeric carrier. Polymeric materials often require heating during production, but a cool impregnation is a preferred procedure. One example is the use of water-based resin systems such as modeling dough that is comprised of gelled poly vinyl alcohol, water, and filler. An alcohol solution of semiochemicals is added to the modeling dough to achieve a semi-liquid consistency which can be formed into desired sizes and shapes. Upon the evaporation of the alcohol and water, the poly resin serves to bind the component into a solid and durable polymer that contains a high concentration of semiochemicals.

Another example of cool impregnation involves diluting an epoxy resin with an organic solvent (such as acetone) solution of semiochemicals. Upon evaporation of the solvent, a hardener is added to the impregnated epoxy resin, and it is shaped into desired dimensions.

Microencapsulation procedures may also be used if they do not cause excessive heating or chemical reactions that would degrade semiochemicals. For example, microencapsulated materials can be mixed with plastics and molded into a desired shape.

Another option is to use physical impregnation by saturating polymer absorbents with solutions of semiochemicals. Examples of such absorbents include, but are not limited to, cleanroom wipes made of meltblown polypropylene, and various grades of absorbent papers made of filament polyester. Mesh-like materials can also be used. These non-cellulose absorbents are made of polymers and will not degrade by exposure to chemicals or microbes. These materials can absorb a large quantity of semiochemicals that can be slowly released into adjacent soil.

These procedures are merely exemplary; other procedures can be used to impregnate a high concentration of semiochemicals into the polymer without causing significant degradation of the semiochemical. Once impregnated, semiochemicals are protected by the polymer materials, yet some semiochemicals are slowly released into the adjacent soil to create a semiochemical gradient that causes termites to make oriented movement toward the sources. The release rate can be manipulated with different types of polymers and the like.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Preparation of Fungi Decay Extract

Spruce (*Picea* sp.) boards (13 by 8 by 0.5 cm) were inoculated with brown-rot fungi, *Gloeophyllum trabeum*, and stored at 25° C. and >90% relative humidity for 1-2 months, during which the wood weight loss due to fungal decay exceeded 50%. The decayed wooden boards were soaked in an acetone solution for >48 hrs, and the acetone extract was condensed at room temperature to yield the desired concentration.

EXAMPLE 2

Open Air Choice Test

The biological activity of the extract was first tested in a petri dish (9 cm diameter and 1 cm high). Two pieces of filter papers (Whatman No. 1, 9 cm diameter) were cut in half and placed side-by-side together in the petri dish without touching each other. One half of the paper received acetone solution of the extract, the other received acetone only. Upon the evaporation of the acetone, both filter papers were moistened with deionized water. Twenty field-collected termites (*Coptotermes formosanus*) were placed in the dish and the numbers of termites present on each filter paper piece were counted 1-2 minutes later. The test was repeated six times. As shown in Table I, most termites preferred to aggregate on paper treated with acetone extract of fungi decay wood than acetone control, indicating the "arrestant" property of the decay extract.

TABLE I

Mean numbers of termites (of the 20 termites) found on a filter paper in a petri dish choice test, number of polymer discs intercepted by termite tunnels in a tunneling choice test.

| Treatment | Petri dish choice test (number of termites) | Tunneling choice test (number of intercepted discs) |
| --- | --- | --- |
| Control | 3.2 ± 1.2 | 0 |
| Paper or disc treated with fungi decay wood extract | 16.8 ± 1.2 | 6 |

EXAMPLE 3

Impregnation of Polymer Disc with Fungi-decay Wood Extract

Polymer discs (3.6 cm diameter) were cut out of a meltblown polypropylene fiber sheet. Acetone solution of fungi-decay wood extract was pipetted onto each disc to yield a concentration (wt/wt) four times higher than those present in fungi decay wood. Control discs were treated with acetone only. The impregnated polymer discs were air dried for 24 hrs before testing.

EXAMPLE 4

Figure 2:
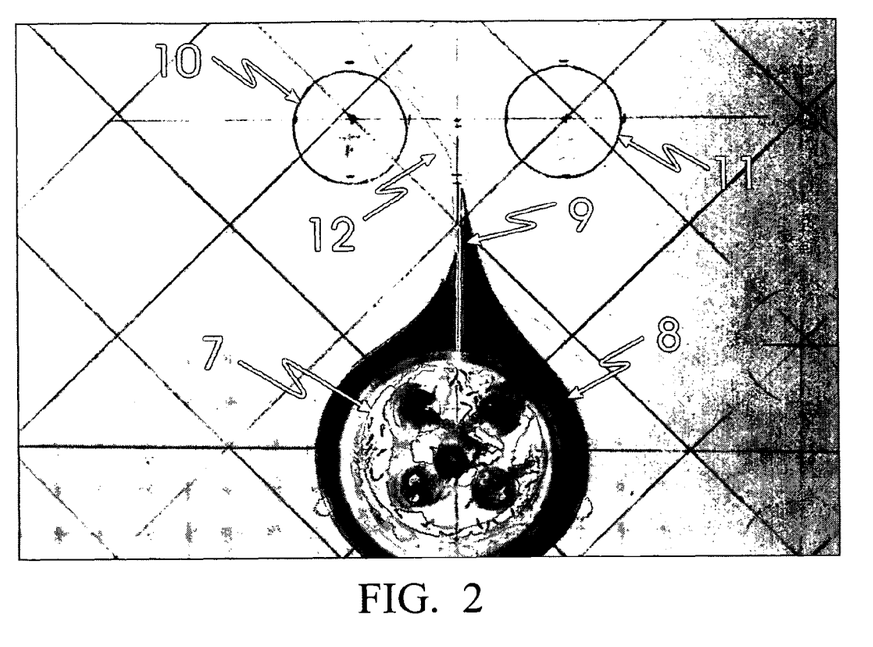
FIG. 2 shows tunneling responses of termites, to treated polymer discs in sand, after being released in a chamber (7) at the center of a 2-dimensional foraging area. Released termites were forced to follow an artificial tunnel ending in a staggered physical guide (9). A pair of polymer discs, one impregnated with acetone extract of fungus-decayed wood (10) and the other an acetone-only control (11), were placed at 3 cm apart in sand near the end of the physical guide. Upon exiting the physical guide, termite tunneling (12) was "directed" toward the disc treated with fungi-decay extract.

Tunneling Choice Test for Termites Foraging in Soil using a Two-Dimensional Foraging Arena A choice test was done in a laboratory arena to investigate the effects of treated polymer discs on termites tunneling in soil. The arena was constructed of two sheets of transparent Plexiglas (50×50 cm) separated from each other by four Plexiglas laminas (50×2.5×0.2 cm) placed between the outer margins. As shown in FIG. 2, four access holes (1 cm diameter) were drilled surrounding the center of the upper sheet and covered with a termite release chamber (7). As shown, the chamber was 5 cm high with a 6 cm diameter. A plastic ring spacer (8) (0.2 cm thick, 8 cm diameter, and 1 cm wide) was placed beneath the release chamber to separate termites from the rest of the arena. The 0.2 cm gaps between the Plexiglas sheets were filled with 400-500 g of sifted sand (150-500 μm sieves; Play Sand Bonsal, Inc.) and moistened with 125-150 ml of deionized water. Two hundred fifty workers of the Formosan subterranean termite (plus 15 soldiers) were released into the chamber and were forced to follow an artificial tunnel ending in a staggered physical guide as part of the plastic (9) before exit into the sand in the arena. When encountering a hard object while tunneling in soil, termites follow the object's physical guideline. This experimental device took advantage of termite physical-guideline-following behavior. My previous observations indicated that when the physical guide ended abruptly, as was arranged by the sharp tips of the staggered ends, termites continued to tunnel in the same general direction in the sand. Thus, after following the provided guide, termites formed a more or less straight tunnel for another 5-10 cm. Two polymer discs, one impregnated with acetone extract of fungi decay wood (10) and other acetone only control (11), were placed 3 cm apart in sand at an equal distance from the end of the physical guide. Termite tunneling geometry was recorded daily, and the number of discs intercepted by termites was counted. The experiment was repeated 6 times.

The results showed that in all six experiments (Table I), termite tunnels were directed toward the polymer disc impregnated with fungus-decayed wood extract (12). The results clearly demonstrated that when imbedded in sand, sufficient quantity of "attractants" permeated out of the treated disc to cause termites to make orientated movement toward the sources of the attractants.

Subterranean termites forage in soil, and the ability of semiochemicals intended to "attract" termites have not heretofore been demonstrated to cause termite tunneling to make oriented movement toward the source of the attractants. "Attractants" for termites heretofore described in the art typically employed an open air choice test as described in Example 1; this only demonstrates palatability or arrestant property of the bait instead of the ability of a semiochemical to change the direction of termite tunneling. This is the first time the "attractant" property of semiochemicals was demonstrated to cause termites to change their tunneling direction toward the sources.

EXAMPLE 5

Measuring the Distance of "Attractant" Effects of Fungus-Decay Extract in Soil

Figure 3:
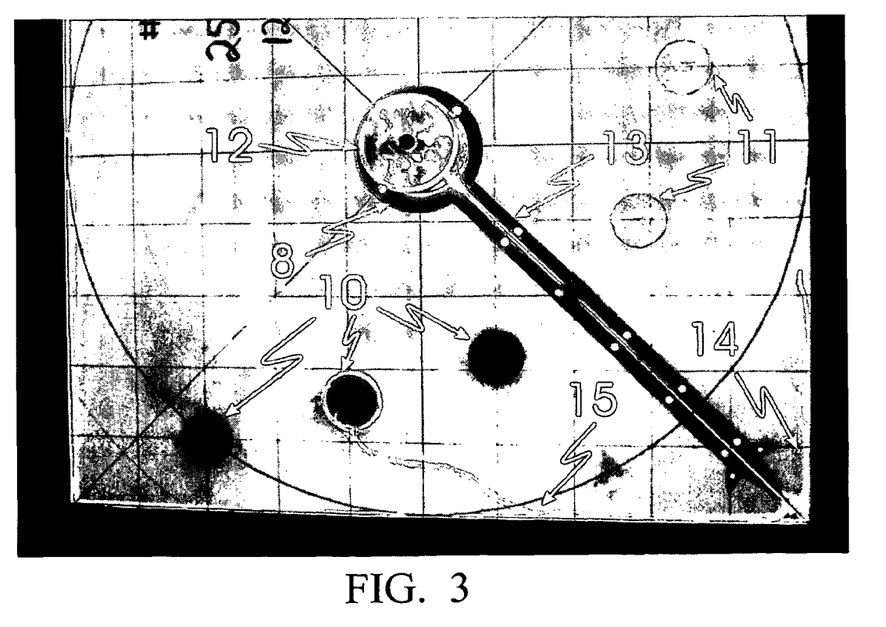
FIG. 3 shows a termite tunnel that departed from the arena edge and was "directed" to a polymer disc impregnated by fungus-decayed wood extract (10). Termite tunneling was not affected by the control discs treated with acetone only (11). The distance of "attraction" by the polymer disc was measured between the point where the termite tunnel departed from the arena edge (15) and the intercepted disc.

The distance by which the impregnated polymer "attracts" termites foraging in soil was measured using another configuration of the 2-dimensional foraging arena. The test was conducted for two termite species, *Coptotermes formosanus*, and eastern subterranean termite, *Reticulitermes flavipes*. As illustrated by FIG. 3, termites released at the center chamber (12) were forced to follow a long artificial tunnel (13) to exit at the corner of the arena. Previous observation indicated that when termites reached the arena edge, they usually followed the edge guideline, and tunneled more or less in a straight line along the edge (14). Three polymer discs were each imbedded in sand along two sides of the arena, each at distances of 9 cm, 6 cm, and 3 cm from the edge. Three discs at one side were treated with acetone extract of fungi-decayed wood as described in Example 3 (10), while the other 3 were treated with acetone only (11). The distance between the point where termite tunnel departed from the arena edge (15) and the intercepted disc was measured. The experiment was repeated six times each for both *C. formosanus* and *R. flavipes*.

Termite tunneling remained along the edge on the sides lined with control discs, while termites tunneled toward at least one of the treated discs when traveling along the other side lined with treated discs (FIG. 3). For *C. formosanus*, at least one treated disc was intercepted by termite tunnels for all replicates, while *R. flavipes* intercepted at least one treated disc for most of the replicates (Table II). The mean distance of the tunneling that departed from the edge to the treated discs was 9-10 cm for both termite species (Table II). These results demonstrate that semiochemicals of the extract could permeate >10 cm (in some replicates >20 cm) from the polymer disc to "attract" termites foraging in soil. Thus, it has been demonstrated that attractant-impregnated polymers, as part of a monitoring procedure, can be used to greatly extend the detection range of a monitoring station.

TABLE II

Number of polymer discs intercepted by termite tunnels and distance (cm) of "attractant" effects of fungal decay extract as measured by the tunnel length intercepting a polymer disc. Figures are mean (±SE) of 6 replicates for both termite species.

| Termite Sp. | Treatment | Number of intercepted disks | Mean distance (cm) of intercepted tunnel |
|---|---|---|---|
| C. formosanus | Control disc | 0 ± 0 | 0 ± 0 |
| | Treated disc | 1.0 ± 0.6 | 9.7 ± 4.7 |
| R. flavipes | Control disc | 0 ± 0 | 0 ± 0 |
| | Treated disc | 0.7 ± 0.5 | 10.7 ± 10.2 |

REFERENCES

Matsumura, F., A. Tai, & H. C. Coppel. 1969. Termite trail-following substance, isolation and purification from *Reticulitermes virginicus* and fungus-infected wood. *J. Econ. Entomol.* pp. 599-603.

Metcalf, R. L. & R. A. Metcalf. 1975. Attractants, repellents, and genetic control in pest management, pp. 275-306, In: Metcalf, R. L. & W. Luclmann [eds], *Introduction to Insect Pest Management*, John Wiley & Sons, New York.

Shorey, H. H. 1977. Interaction of insects with their chemical environment, pp. 1-5, In: Shorey, H. H. & J. J. McKelvey, Jr. [eds], *Chemical Control of Insect Behavior*, John Wiley & Sons, New York.

The invention claimed is:

1. A semiochemical delivery system for attracting termites wherein said system comprises a bait station, holding a cellulose source, and at least one durable, polymeric piece, wherein said piece is made of a non-cellulose polymer that holds a termite-attracting semiochemical that is gradually released into soil to form a semiochemical gradient in the soil when said polymeric piece is deployed in soil, wherein said polymeric piece is external to said bait station so that said semiochemical gradient leads termites foraging in the area to said bait station.

2. The delivery system of claim 1 wherein said polymeric piece is attached to said bait station.

3. The delivery system of claim 1 wherein said polymeric piece is in soil within two feet of said bait station.

4. The delivery system of claim 1 wherein said polymeric piece is a sleeve fitted around said bait station.

5. The delivery system of claim 4 wherein said sleeve is made of an absorbent foam.

6. The delivery system of claim 1 wherein bait station is a hermetically sealed bait pouch made from a flexible material containing therein a toxicant-containing matrix.

7. The delivery system of claim 1 wherein said bait station is a durable station housing wherein an opening is defined in said durable station housing and said opening permits a removable cellulose source to be placed within said housing and said opening provides above-ground access to said cellulose source when said cellulose source is placed within said station housing.

8. The delivery system of claim 7 further comprising a removable cellulose source within said station housing.

9. The delivery system of claim 8 wherein said cellulose source is a monitoring device.

10. The delivery system of claim 8 wherein said cellulose source is a toxicant-containing matrix.

11. The delivery system of claim 1 wherein said polymer is impregnated with said semiochemical.

12. The delivery system of claim 1 wherein said semiochemical is a pheromone.

13. The delivery system of claim 1 wherein said semiochemical is water-soluble.

14. The delivery system of claim 1 wherein said semiochemical is extract of fungal-decayed wood.

\* \* \* \* \*